US009855346B2

(12) United States Patent
Fang et al.

(10) Patent No.: US 9,855,346 B2
(45) Date of Patent: Jan. 2, 2018

(54) FLUORESCENT DYE COMPOSITIONS AND USES THEREOF

(71) Applicant: Chang Gung University of Science and Technology, Guishan Dist., Taoyuan (TW)

(72) Inventors: Chia-Yu Fang, Taoyuan (TW); Chih-Jen Wen, Baoshan Township, Hsinchu County (TW)

(73) Assignee: Chang Gung University of Science and Technology, Taoyuan (TW)

(*) Notice: Subject to any disclaimer, the term of this patent is extended or adjusted under 35 U.S.C. 154(b) by 0 days.

(21) Appl. No.: 14/932,001

(22) Filed: Nov. 4, 2015

(65) Prior Publication Data

US 2016/0129136 A1    May 12, 2016

Related U.S. Application Data

(60) Provisional application No. 62/076,136, filed on Nov. 6, 2014.

(51) Int. Cl.
*A61K 9/00*    (2006.01)
*A61K 49/00*    (2006.01)

(52) U.S. Cl.
CPC ...... *A61K 49/0032* (2013.01); *A61K 49/0082* (2013.01)

(58) Field of Classification Search
CPC .................................................. A61K 40/0032
See application file for complete search history.

(56) References Cited

FOREIGN PATENT DOCUMENTS

CN    102166189 A    *    8/2011

OTHER PUBLICATIONS

Machine translation of CN 102166189 A, May 2016.*
Li, et al. Direct labeling and visualization of blood vessels with lipophilic carbocyanine dye DiI; Nature Protocols, vol. 3 No. 11, 2008 (pp. 1703-1708).
Shu-Hui Hsu, et al., "Physicochemical characterization and in vivo bioluminescence imaging of nanostructured lipid carriers for targeting the brain: apomorphime as a model drug", Nanotechnology 21 (2010), 12 pgs.
Isabelle Texier, et al., "Cyanine-loaded lipid nanoparticles for improved fluorescence imaging in vivo fluorescence imaging", Journal of Biomedical Optics 14(5), (Sep./Oct. 2009), 11 pgs.

* cited by examiner

*Primary Examiner* — Paul W Dickinson
(74) *Attorney, Agent, or Firm* — Muncy, Geissler, Olds & Lowe, P.C.

(57) ABSTRACT

Compositions comprising one or more nanoparticles, wherein the nanoparticles encapsulate fluorescence dyes are disclosed. In one embodiment, the nanoparticle comprises triterpene. In another embodiment, the nanoparticle comprises triterpene and fatty ester. Methods for performing a diagnostic or a therapeutic procedure comprising administering to a subject an effective amount of the compositions of the present invention or carbocyanine dyes are also provided.

13 Claims, 6 Drawing Sheets

FLUORESCENT DYE COMPOSITIONS AND USES THEREOF

CROSS REFERENCE TO RELATED APPLICATIONS

This application claims priority under 35 U.S.C. 119(e) to U.S. Provisional Patent Application No. 62/076,136 filed on Nov. 6, 2014, the contents being incorporated by reference in its entirety.

FIELD OF THE INVENTION

The invention relates to compositions useful in optical imaging.

BACKGROUND OF THE INVENTION

Optical imaging, especially in the near-infrared (NIR) wavelengths, is expected to have significant impact for in vivo imaging because of the low absorption of biological molecules, high sensitivity, high spatial and temporal resolution, safety, and low costs.

The resolution of optical imaging relies greatly on the stable, highly specific and sensitive fluorescence probes or dyes. Indocyanine green (commonly known as ICG) is an FDA approved fluorescence dye for use in coronary angiography, evaluation or hepatic function and monitoring blood flow. However, ICG has a very short plasma half-life, thus limiting the imaging time available during its vascular circulation. The use of polymeric and metallic nanoparticle-based fluorescence probes for optical imaging demonstrated enhanced resolution and prolonged half-life in plasma. However, the toxicity of these nanoparticle-based probes is a concern due to the presence of synthetic polymers or toxic metals (S. Keereweer et al., Optical image-guided surgery: where do we stand? *Mol. Imaging Biol.* 2011, 13, 199-207.)

There is still a need for a more effective and safe fluorescence probe for optical imaging of the vasculature and/or the lymphatic system. The present invention addresses this need.

BRIEF SUMMARY OF THE INVENTION

In one embodiment, the present invention relates to compositions comprising one or more nanoparticles, and the nanoparticles comprise one or more triterpenes; and one or more fluorescence dye, wherein said triterpene encapsulates the fluorescence dye.

In another embodiment, compositions comprising one or more nanoparticles, and the nanoparticles comprise squalene; cetyl palmitate; and one or more surface additives selected from phospholipid, PEGylated phospholipid, glyceride and carbocyanine, wherein the ratio of squalene:cetyl palmitate of the composition is about 2.5%:7.5% (v/w) to about 9%:1% (v/w) are disclosed.

The present invention is directed to methods for performing a diagnostic procedure comprising administering to a subject an effective amount of the composition described herein.

Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

FIG. 3A to 3D is an assembly of electron microscopy images illustrating the morphology of the nanoparticles in S1-S4 compositions.

DETAILED DESCRIPTION

As employed above and throughout the disclosure, the following terms, unless otherwise indicated, shall be understood to have the following meanings.

As used herein, the singular forms "a," "an," and "the" include the plural reference unless the context clearly indicates otherwise.

The term "subject" as used herein typically refers to a human or an animal subjected to the methods described herein. It is to be understood that a subject can be a patient with known or suspected disease in need of an optical imaging, but subjects without known or suspected disease, such as research subjects, are also included within the scope of the term "subject."

All numbers herein may be understood as modified by "about."

Figure 1:
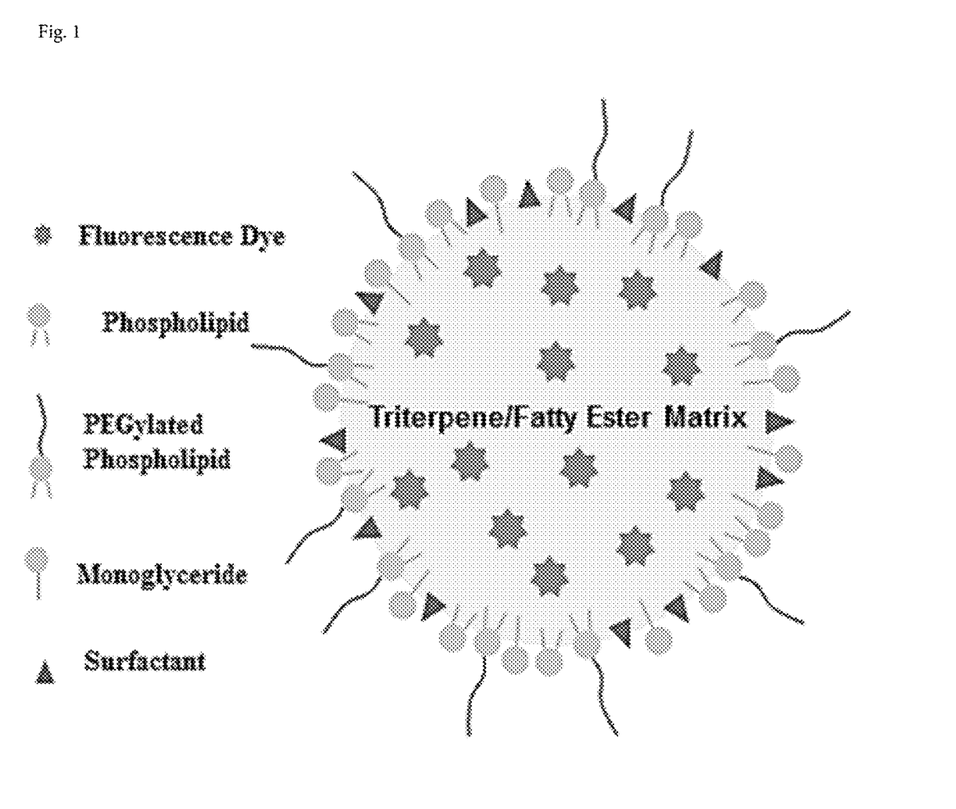
FIG. 1 illustrates schematically the cross section of one embodiment of the present invention.

The present invention provides compositions comprising one or more nanoparticles, wherein the nanoparticles comprise one or more triterpenes, and one or more fluorescence dye, wherein the fluorescence dye is encapsulated in the core of the nanoparticles. In one embodiment, the fluorescence dye is embedded in the triterpene and/or fatty ester core of the nanoparticle, as illustrated in FIG. 1. The fluorescence dye in the composition of the present invention exhibits less fluorescence quenching (higher fluorescence emission), higher signal to noise ratio (better delineation of the images), longer intravascular retention and delayed liver clearance (longer imaging time), deeper tissue penetration depth, and less plasma protein binding and spleen accumulation compare to a fluorescence dye not encapsulated in the nanoparticles.

In certain embodiments, the nanoparticles are suspended in an aqueous solution. In other embodiments, the nanoparticles encapsulate one or more fluorescence dyes In one exemplary embodiment, the nanoparticles in the present invention comprise one or more triterpenes. In another exemplary embodiment, the nanoparticles comprise one or more triterpenes; and one or more fatty esters. In yet another exemplary embodiment, the nanoparticles comprise one or more triterpenes; one or more fatty esters; and one or more surface additives, as illustrated in FIG. 1. In yet another embodiment, the nanoparticles further comprises a ligand for target cell binding.

In certain embodiments, the nanoparticles are substantially free of polymer, synthetic polymer, gas or metal.

Non limiting examples of triterpene include squalene, ambrein and ganoderic acid.

Non limiting example of the fatty ester includes cetyl palmitate (CP).

Non limiting examples of surface additive include phospholipid, PEGylated phospholipid, monoglyceride, surfactant, or any additive that provide steric and electrostatic stabilization of a nanoparticle in an aqueous solution preferably the surface additive of the composition is about 0.1% to about 6.5% (v/w)

In certain embodiments, phospholipid is selected from phosphatidylcholine (PC), soy phosphatidylcholine (SPC), distearoylphosphatidylethanolamine (DSPE), phosphatidylserine, phosphatidic acid, or phosphatidylinositol.

In other embodiments, PEGylated phospholipid is selected from distearoylphosphatidylethanolamine-polyethylene glycol (DSPE-PEG) with an average molecular weight of 2000 to 5000 daltons, or a phospholipid conjugated with mPEG.

Examples of monoglyceride include, but not limited to, palmitinic acid monoglyceride.

Examples surfactant include, but not limited to, Pluronic® F68, commercially available from Sigma-Aldrich (St Louis, Mo., USA).

The ratio of triterpene:fatty ester of the nanoparticle plays an important role in the signal to noise ratio (i.e., contrast or delineation) of fluorescence dye and the depth of tissue penetration. In one embodiment, the ratio of triterpene:fatty ester of the composition is about 2.5%:7.5% (v/w), about 7.5%:2:5% (v/w), or about 9%:1% (v/w). Other ratios are also encompassed by the invention, including ratios of triterpene:fatty ester of the composition of about 1%:9% (v/w); about 1.5%:8.5% (v/w); about 2%:8% (v/w); about 3%:7% (v/w); about 3.5%:6.5% (v/w); about 4%:6% (v/w); about 4.5%:5.5% (v/w); about 5%:5% (v/w); about 5.5%: 4.5% (v/w); about 6%:5% (v/w) about 6.5:3.5% (v/w); about 7%:3% (v/w); about 8%:2% (v/w); about 8.5%:1.5% (v/w); about 9.5:0.5% (v/w).

In one embodiment, the % of fatty ester of the composition is less than about 2%, less than about 1.5%, less than about 1%. In another embodiment, the % of triterpene is about 8% to about 10%, about 8.5% to about 9.5%, about 9%. The lower % of fatty ester in the composition showed a higher signal to noise ratio due to a reduced crystalline lattice of the nanoparticles in the NMR study. Without being bound by any particular theory, a lower % of fatty ester and less crystalline lattice of the nanoparticles means the nanoparticle is deformable and hence, a better adhesion/attachment to the blood vessel wall and a better delineation of the blood vessel during optical imaging.

The nanoparticle may further comprise a ligand, such as a lipid-conjugate of an antibody or a peptide, acts as a targeting moiety to enable the nanoparticle to specifically bind to a target cell bearing a target molecule. Examples of the target molecules include, but are not limited to, epidermal growth factor receptor (EGFR), vascular endothelial growth factor receptor (VEGF), carcinoembryonic antigen (CEA), and erbB-2/neu (HER2).

The compositions to be administered according to some embodiments provided herein can be readily formulated with, prepared with, or administered with, a pharmaceutically acceptable carrier. Such preparations may be prepared by various techniques. Such techniques include bringing into association nanoparticles of the compositions and an appropriate carrier. In one embodiment, the compositions are prepared by bringing nanoparticles of the compositions into association with liquid carriers, with solid carriers, or with both. Liquid carriers include, but are not limited to, aqueous formulations, non-aqueous formulations, or both. Solid carriers include, but are not limited to, biological carriers, chemical carriers, or both.

Some examples of the nanoparticle preparation are described below to illustrate the processes of nanoparticle preparation as they relate to the present invention.

The compositions are administered in an aqueous suspension, an oil emulsion, water in oil emulsion and water-in-oil-in-water emulsion, and in carriers including, but not limited to, creams, gels, emulsions and minipumps, the minipumps being implanted in the vicinity of where composition delivery is required.

The compositions provided herein may anti-oxidants, buffers, bacteriostatic agents, suspending agents, thickening agents, preservatives, co-solvents and viscosity building agents or other therapeutic ingredients. The nanoparticles, the fluorescence dye and the therapeutic agents must be compatible with the other ingredients of the composition and not deleterious to the recipient thereof.

The compositions are administered in an effective amount for performing a diagnostic procedure (such as vascular imaging). The dosage of the composition administered will depend on the severity of the condition being treated, the type of imaging used, the particular formulation, and other clinical factors such as weight and the general condition of the subject and route of administration. In one exemplary embodiment, the amount of fluorescence dye administered corresponds to about 0.005% (v/w) of the composition. In another exemplary embodiment, the volume of the composition administered is about 2 ml. Useful dosages of the composition provided herein are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

In accordance with the methods provided herein, the composition is delivered by any of a variety of routes including, but not limited to, injection (e.g., subcutaneous, intramuscular, intravenous, intra-arterial, intraperitoneal, intradermal); cutaneously; dermally; transdermal; oral (e.g., tablet, pill, liquid medicine, edible film strip); implanted osmotic pumps; suppository, aerosol spray, topical, intra-articular, ocular, nasal inhalation, pulmonary inhalation, impression into skin and electroporation. In one embodiment, the compositions of the present invention can be administered as a solution by intravenous injection.

The compositions may be administered in a single dose or in multiple doses over a period of time appropriate to the procedure being carried out. The compositions may conveniently be administered at appropriate intervals, for example, once a day, twice a day, three times a day, once every second day, once every three days or once every week, over a period of at least 3 months, at least 1 year, or until the symptoms and signs of the disease resolved.

Fluorescence dyes can emit light upon light excitation. Based on molecular complexity and synthetic methods, fluorescence dyes could be generally classified into four categories: proteins and peptides, small organic compounds, synthetic oligomers and polymers, and multi-component systems.

Non limiting examples of fluorescence dyes include: xanthene derivatives, such as fluorescein, rhodamine, Oregon green, eosin, and Texas red, cyanine derivatives such as indocarbocyanine, carbocyanine, thiacarbocyanine, indocyanine and merocyanine; naphthalene derivatives such as dansyl and prodan derivatives; coumarin derivatives; oxadiazole derivatives such as pyridyloxazole, nitrobenzoxadiazole and benzoxadiazole; anthracene derivatives such as anthraquinones, including DRAQ5, DRAQ7 and CyTRAK Orange; pyrene derivatives such as cascade blue; oxazine derivatives such as Nile red, Nile blue, cresyl violet and oxazine 170; acridine derivatives such as proflavin, acridine orange and acridine yellow; arylmethine derivatives such as auramine, crystal violet and malachite green; and tetrapyrrole derivatives such as porphin, and phthalocyanine and bilirubin.

Cyanine dyes are cationic molecules in which two terminal nitrogen heterocyclic units are linked by a polymethine bridge as shown by Formula (I):

Formula (I)

wherein R is independently a $C_1$-$C_6$ alkyl group, which may be straight or branched, or a C3-C10 mono, bicyclic or fused carbocyclic ring, and n is 1-4. The heterocyclic units may be an aromatic or non-aromatic mono, bicyclic or fused ring containing 1-4 ring nitrogens and 4-9 ring carbons. Non-limiting examples of heterocyclic units are pyridyl, piperidinyl, indolyl and dihydroindolyl.

Cyanine dyes are lipophilic cations and possess a wide range of absorption, between the visible and infrared regions of the electromagnetic spectrum. Due to these properties, cyanine dyes have been extensively employed in optical imaging of nerve membrane potential. Cyanine dyes include, by way of illustration and not limitation, hydrocyanines, carbocaynines, dicarbocyanine, tricarbocyanine, indocyanine, and derivatives thereof. The term "derivative" is meant to include modifications to the cyanine dye by addition of chemical structure (such as, e.g., rings structures) or substituents (such as, e.g., alkyl, aryl, and halogen) to the cyanine dye while still retaining the fluorescence activity.

Figure 2:
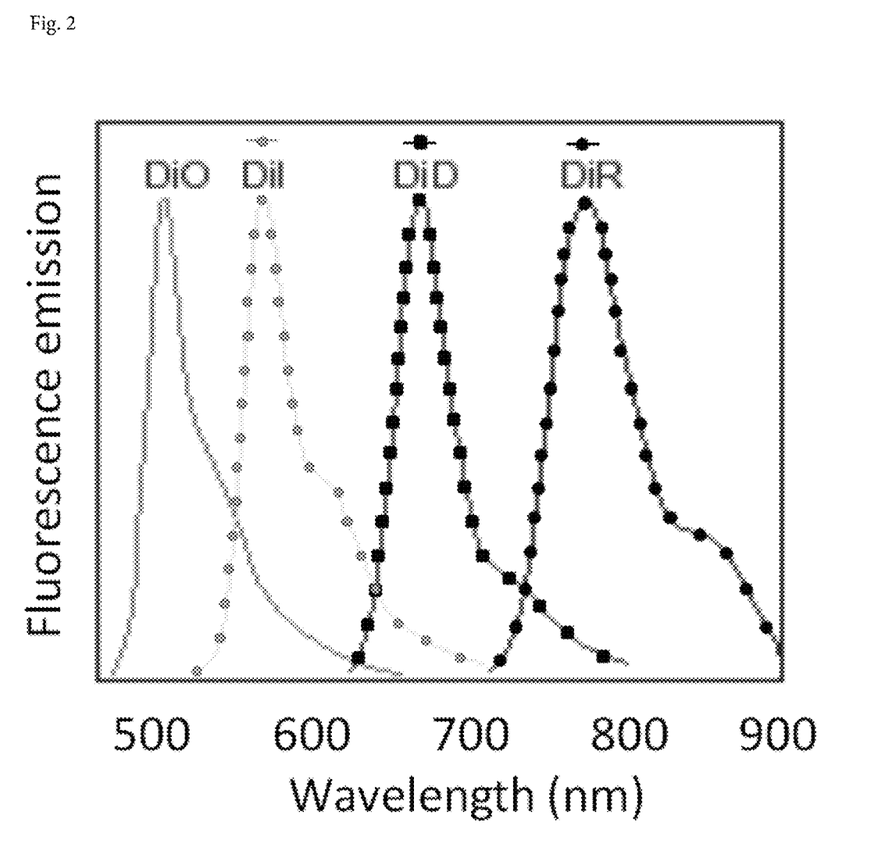
FIG. 2 illustrates the fluorescence emission of the DiO, DiI, DiD and DiR dyes in their respective wavelengths.
Figure 3A:
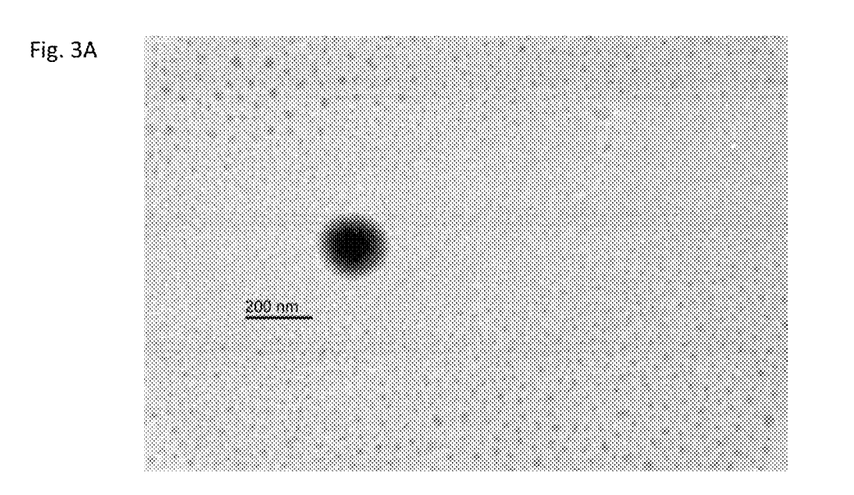
FIG. 3A is a photograph of the nanoparticle in S1 composition.
Figure 3B:
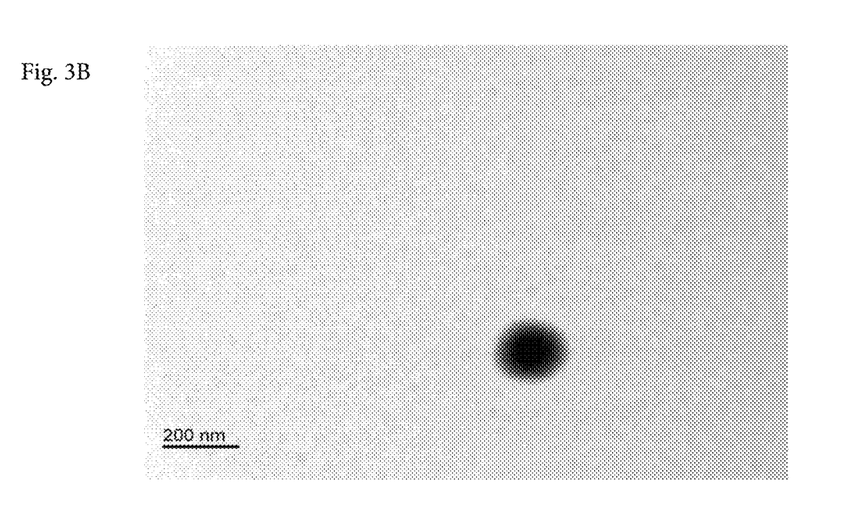
FIG. 3B is a photograph of the nanoparticle in S2 composition.
Figure 3C:
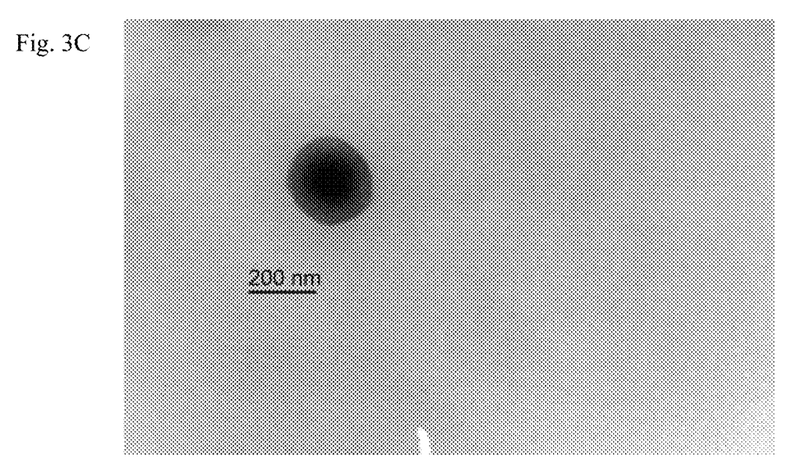
FIG. 3C is a photograph of the nanoparticle in S3 composition.
Figure 3D:
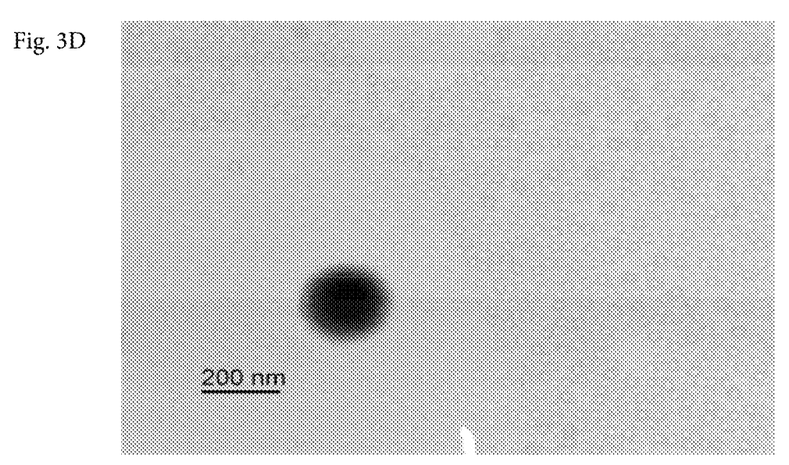
FIG. 3D is a photograph of the nanoparticle in S4 composition.

Some of the cyanine dyes operate in the NIR range (700-900 nm), such as indocyanine (e.g., ICG) and DiR carbocyanine (e.g., 1'-Dioctadecyl-3,3,3',3'-tetramethyl-indotricarbocyanine iodide), while others operate in the visible orange red wavelengths, such as DiI carbocyanine (e.g., 1,1'-dioctadecyl-3,3,3',3'-tetramethylindocarbocyanine perchlorate) or the visible green wavelength (e.g., DiO and its derivatives). 3,3'-dipentylthiodicarbocyanine (DiS-$C_3$(5)) and 3,3'-diethylthiodicarbo cyanine iodide (DiS-$C_2$-(5), collectively known as DiS, are some examples of thio-containing cyanine dye. FIG. 2 illustrates the fluorescence emission of the DiO, DiI, DiD and DiR cyanine dyes in its respective wavelength.

The carbocyanine dyes tend to self-aggregate and photobleach (due to the interaction with dissolved oxygen) in an aqueous solution, resulting in untypical fluorescence emission during optical imaging. These drawbacks limited the use of these carbocyanine dyes in vascular imaging. In one embodiment, the present invention provides the use of carbocyanine dyes for optical imaging of the vasculature. In another embodiment, the present invention provides the use of carbocyanine dyes, encapsulated in the core of the nanoparticles described herein, for optical imaging of the vasculature. In an exemplary embodiment, the carbocyanine dye is DiR, DiI or DiS.

Methods of using the composition encapsulating a fluorescence dye, or a carbocyanine dye in a diagnostic procedure, such as optical imaging of the vasculature and/or lymphatics, blood flow and blood volume change, or optical imaging of perfusion or wound healing in a subject after organ transplantation, plastic surgery, and reconstructive surgery are provided herein.

The procedures described herein also encompass research methods and uses, including in vitro and ex vivo methods of optical imaging or drug delivery to a cell, a tissue or a subject.

The composition with a fluorescence dye maybe administered concomitantly or non-concomitantly with a therapeutic agent. In one embodiment, the fluorescence dye and the therapeutic agents are encapsulated in the same nanoparticle for administering.

The use of the composition in optical imaging enhances the fluorescence signal of the fluorescence dye. In one embodiment, the optical imaging uses a wavelength in the region of about 380 to about 1000 nm. In another embodiment, the optical imaging uses a wavelength in the NIR region. In yet another embodiment, the optical imaging uses a wavelength in the region of about 700 to about 900 nm.

Embodiments of the present invention are illustrated by the following examples, which are not to be construed in any way as imposing limitations upon the scope thereof. During the studies described in the following examples, conventional procedures were followed, unless otherwise stated. Some of the procedures are described below for illustrative purpose.

Description of Materials and Methods Used in the Examples

Squalene, Pluronic F68, and (3-(4,5)-dimethylthiazol-2-yl)-2,5-diphenyltetrazolium bromide (MTT) were purchased from Sigma-Aldrich (St Louis, Mo., USA). Cetyl palmitate (CP) was purchased from Acros (Geel, Belgium). Hydrogenated soybean phosphatidylcholine (SPC, Phospholipon® 80H) was obtained from American Lecithin (Oxford, Conn., USA). Distearoylphosphatidylethanolamine-polyethylene glycol (DSPE-PEG) with an average molecular weight of 5000 was purchased from Nippon Oil (Tokyo, Japan). Myverol 18-04K (palmitinic acid monoglyceride) was purchased from Quest (Naarden, the Netherlands). 1,1'-Dioctadecyl-3,3,3',3'-tetramethyl-indotricarbocyanine iodide (DiR) was commercially available from AAT Bioquest (Sunnyvale, Calif., USA). Zoletil® 50 was from Virbac (Carros, France).

Measurement of Nanoparticle Size and Zeta Potential

The diameter and zeta potential of the nanoparticles of the compositions were measured by Nano ZS90 (Malvern, Worcestershire, UK).

Nuclear Magnetic Resonance (NMR)

The mobility of CP in the compositions was evaluated by NMR, by measuring the line widths of half-amplitude (Hz) of methylene protons. Compositions were diluted with deuterium oxide by 3-fold. Neat CP was diluted with chloroform-d. The compositions were loaded into NMR tubes and their $^1$H-NMR spectra were examined by Avance 400 spectrometer (Bruker, Bremen, Germany).

Transmission Electron Microscopy (TEM)

The morphology of the nanoparticles of the compositions was examined using H-7500 electron microscopy (Hitachi, Tokyo, Japan).

Fluorescence Intensity of the Compositions

The fluorescent intensity of the compositions was determined with or without ham slice, the formal was used to mimic human tissues. The ham slice with a thickness of about 1.6 cm was placed above a tube containing the compositions. The fluorescence activity of the compositions through the ham slice was detected by Pearl® Impulse system (Li-Cor, Lincoln, Nebr., USA) at an emission wavelength of 800 nm.

Animals

Male Sprague-Dawley rats aged 8~10 weeks was supplied by Lasco (Taipei, Taiwan). Animal experimental protocol was approved by the Institutional Animal Care and Use Committee of Chang Gung University, Taiwan. The rats had free access to water and food at all time.

In Vivo and Ex Vivo Optical Imaging

The rats were anesthetized and injected with the compositions of the present invention or the control solution (dimethyl sulfoxide:Tween 80:normal saline=4:2:4) at a DiR dose of 40 μg/kg via femoral vein. In vivo real-time imaging was acquired using Pearl® Impulse at NIR wavelength. Rats were sacrificed 4 h post-injection. The following organs were collected and washed with normal saline: skin, muscle, heart, lungs, liver, spleen, and kidneys. The fluorescence intensity in these organs was assessed Ex Vivo by Pearl® Impulse.

Cytotoxicity Study Using Neutrophils

LDH release from neutrophils is a surrogate marker for cytotoxicity. The release of LDH was measured by a commercially available LDH kit (Promega, Madison, Wis., USA). Neutrophils were isolated from a blood sample taken from a healthy human subject (20~30 years old) using a protocol approved by the Institutional Review Board at Chang Gung Memorial Hospital, Taiwan. Cytotoxicity was represented by LDH released/total LDH released (measured by lysing neutrophils with 0.1% Triton X-100 at 37° C. for 30 min).

Cytotoxicity Study Using Human Umbilical Vein Endothelial Cells (HUVECs)

The HUVECs ($10^4$ cells/ml) were seeded in 96-well plates for a 24-h culture. Compositions of the present invention were diluted with culture medium at the following ratios: 1/1000, 1/100, 1/10, and 1/2, incubated with HUVECs for 24 h at 37° C., followed by incubation with 5 mg/ml MTT in PBS for 2 h. The supernatant was detected by ultraviolet spectrophotometer at 595 nm.

Statistical Analysis

Statistical analysis was performed using unpaired t-test. The post hoc Newman-Keuls test was utilized to check individual differences between groups. A 0.05 level of probability was taken as the level of significance.

Example 1: Preparation of the Compositions

The composition contained a combination of a lipid phase and an aqueous phase. The lipid phase comprised 10% (v/w) of squalene/CP mixture; 0.2% (v/w) of SPC; 0.2% (v/w) of DSPE-PEG, 0.5% (v/w) of Myverol; and 0.005% of DiR dye. The aqueous phase comprised water (84.1%) and Pluronic F68 (5%).

Both lipid and aqueous phases were heated at 85° C. for 15 min. The aqueous phase was subsequently added to lipid phase and homogenized (Pro250, Pro Scientific, Monroe, Conn., USA) at 12000 rpm for 10 min., and further mixed for 10 minutes using probe sonicator (VCX600, Sonics and Materials, Newtown, Conn., USA). The volume of the final composition was 10 ml.

Example 2: Physicochemical Properties of the Compositions

Table 1 shows the size, zeta potential, and line width of NMR half-amplitude of the compositions with various squalene/CP ratio (S1 composition comprised 2.5% (v/w) of squalene and 7.5% (v/w) of CP; S2 composition comprised 7.5% (v/w) of squalene and 2.5% (v/w) of CP; S3 composition comprisec 9% (v/w) of squalene and 1% (v/w) of CP; S4 composition comprised 10% (v/w) of squalene only). The CP-containing compositions, such as S1, S2, and S3, can be classified as nanostructured lipid carriers (NLCs) whereas the CP-free composition, such as S4, is classified as a nanoemulsion. Table 1 illustrates the particle size, polydispersity index (PDI), zeta potential, and line width at half amplitude of S1-S4 compositions.

TABLE 1

The characteristics of S1-S4 compositions

| Composition | Squalene/cetyl palmitate % (v/w) | Size (nm) | PDI | Zeta potential (mV) | Line width (Hz) |
|---|---|---|---|---|---|
| S1 | 2.5:7.5 | 208.03 ± 1.87 | 0.23 ± 0.01 | −32.13 ± 2.53 | 8.43 |
| S2 | 7.5:2.5 | 195.48 ± 5.23 | 0.21 ± 0.01 | −32.98 ± 3.85 | 14.49 |
| S3 | 9:1 | 193.77 ± 4.15 | 0.21 ± 0.01 | −39.63 ± 0.85 | 16.19 |
| S4 | 10:0 | 194.37 ± 1.87 | 0.23 ± 0.01 | −32.06 ± 2.03 | Not applicable |

Each value represents the mean ± SD (n = 3).

The diameters of the nanoparticles in S2, S3, and S4 compositions were about 194 nm, which was significantly smaller (p<0.05) than that of S1 composition, which is about 208 nm. All of the compositions had an PDI value of <0.25, indicating that nanoparticles of the compositions were homogeneous in size (PDI less than 0.3 is considered homogeneous in size). The zeta potential of S1, S2, and S4 compositions was about −32 mV, and comparable (p>0.05) to each other, whereas S3 composition has a slight negative shift of the zeta potential (−40 mV). The mobility of solid fatty ester in lipid cores of the CP-containing compositions was examined by proton NMR. The line width of signals for neat CP was 3.50 Hz. The compositions with a lower CP % (v/w) displayed a higher line width (S3>S2>S1), indicating a reduced crystalline lattice of the nanoparticles in the composition with a lower CP % (v/w).

Example 3: Transmission Electron Microscopy (TEM) Assessment of the Compositions The morphology of the nanoparticles in S1~S4 compositions was assessed by TEM, as illustrated in FIG. 3A to 3D, respectively. The nanoparticles of S1-4 compositions are spherical with a smooth surface. The fluorescence molecules (DiR) were encapsulated in the core of the nanoparticles of the S1-S4 compositions, due to the extremely lipophilic characteristic of DiR (log P=17.4).

Example 4: Storage Stability of the Compositions

The storage stability of S1-S4 compositions was evaluated after 8 weeks of storage at 4° C. and 40° C. in 75% relative humidity). The percentage of change (%) in particle size and zeta potential (surface charge) from baseline is summarized in Table 2.

TABLE 2

The percentage of change in particle size and zeta potential of S1-S4 compositions after 8 weeks storage at 4 and at 40° C.

| Formulation | Size (nm) at 4° C. | Size (nm) at 40° C. | Zeta potential (mV) at 4° C. | Zeta potential (mV) at 40° C. |
|---|---|---|---|---|
| S1 | 1.69 ± 0.01 | −2.43 ± 0.01 | −4.80 ± 0.13 | 9.00 ± 0.37 |
| S2 | 0.92 ± 0.02 | −3.30 ± 0.02 | 0.21 ± 0.003 | 44.44 ± 0.35 |
| S3 | −4.00 ± 0.04 | −0.36 ± 0.007 | 8.65 ± 0.25 | 44.81 ± 0.18 |
| S4 | −0.71 ± 0.008 | −0.15 ± 0.001 | 17.85 ± 0.10 | 62.20 ± 1.15 |

Each value represents the mean ± SD (n = 3)

After 8 weeks of storage at 4° C. and at 40° C., there was a slight change of particle size (<5%) for all compositions. The zeta potential of S1-S4 compositions did not change significantly after 8 weeks of storage at 4° C. At 40° C. storage, the zeta potential of S1 composition increased by 9%, indicating a superior storage stability with a higher % of CP. The results show that S1-S4 compositions are stable for up to 8 weeks at 4° C. storage. The storage of S1-S4 compositions at 4° C. is easier and more convenient than the storage of DiR at −20° C.

Example 5: Fluorescence Intensity of the Compositions

The fluorescence intensity of S1-S4 compositions (without a ham slice) is comparable to that of the control DiR solution, indicating the preservation of fluorescence intensity of DiR with nanoparticle encapsulation. In addition, S1-S4 compositions displayed a stronger fluorescence signal at NIR wavelength relative to the control DiR solution.

Figure 4:
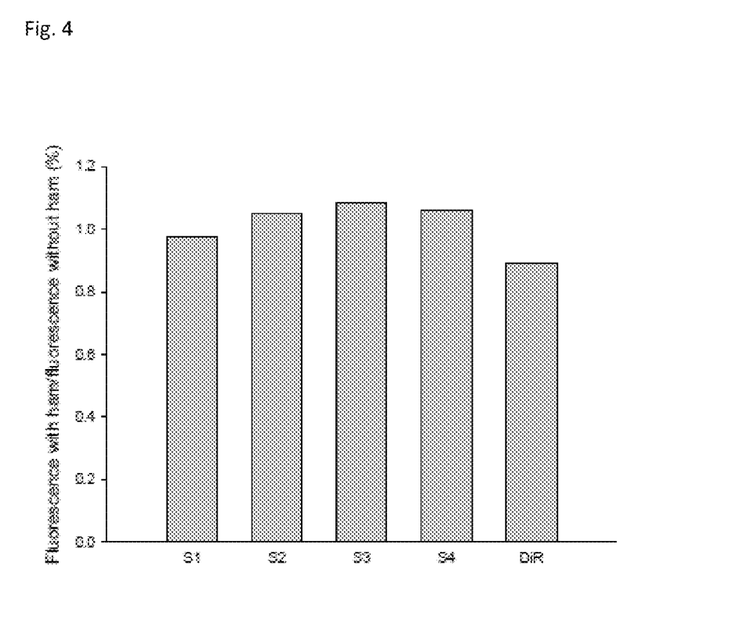
FIG. 4 is bar graph illustrating the % of fluorescence with a ham slice/fluorescence without a ham slice of S1-S4 compositions and the DiR control solution (DiR).

The fluorescence intensity of S1-S4 compositions were evaluated though a ham slice, which simulated human tissues. The fluorescence intensity of S1-S4 compositions could be visualized below the 1.6 cm thick ham slice. FIG. 4 shows the ratios of the fluorescence intensity with a ham slice/fluorescence without a ham slice of S1-S4 compositions and the control DiR solution, analyzed by normalization. DiR retained a ~1% fluorescence after blocking by tissues. S1 composition (with a higher CP %) and the control solution demonstrated a lower tissue penetration of the fluorescence signal than that of S2, S3 and S4 compositions. S3 composition (with a lower CP) shows a better fluorescence signal tissue penetration than S2 and S1 compositions (with a higher % CP).

The results show S1-S4 compositions minimize fluorescence quenching, emit fluorescence signals and are suitable for in vivo fluorescence optical imaging with deep tissue penetration.

Example 6: In Vivo and Ex Vivo Optical Imaging of the Compositions

In Vivo optical images were taken after ICG, control DiR solution (with 40% v/w dimethyl sulfoxide) and S1-S4 compositions were administered into the rats via intravenous (IV) injection.

The images showed a rapid distribution of fluorescence activity throughout the body within 1 min of IV injection of ICG, DiR control solution and S1-S4 compositions.

Imaging Time: The imaging time of ICG was about 5 minutes. The S1-S4 compositions displayed fluorescence activity in large and small vessels, up to 60 min after the injection. The imaging time for microvasculature and lymphatic system, using DiR control solution, is about 120 minutes or more (i.e., between 120 to 240 minutes after IV injection of DiR dye).

The in vivo signal-to-noise ratio: S1 and S2 compositions have a higher fluorescence intensity, a higher background fluorescence activity, and a lower signal-to-noise ratio, whereas the signal to noise ratio was significantly increased in S3 and S4 compositions compared to S1 and S2 composition, indicating S3 and S4 compositions provide a better delineation of the images. The DiR control solution has a lower fluorescence signal and a higher background fluorescence activity (hence, a lower signal-to-noise ratio) compared to S3 and S4 compositions. Although DiR control solution, S1 and S2 compositions have a lower signal-to-noise ratio compare to S3 and S4 compositions, the signal-to-noise ratio of DiR control solution, S1 and S2 compositions are considered adequate for optical imaging of the vasculature and/or lymphatics.

Liver Clearance: The fluorescence intensity of S1 and S2 compositions could be detected in the liver 30 and 60 min post-injection, respectively. The fluorescence intensity of S3 and S4 compositions were detectable in the liver 120 min post-injection. The fluorescence signal of the control DiR solution could be detected in the liver 30-120 minutes post injection whereas similar emission was detected in the liver within 5 minutes after the IV injection of ICG. The encapsulation of the DiR dye by the nanoparticles of the present invention (i.e., S1-S4 compositions) delays the liver clearance of the DiR dye.

Biodistribution/Blood Flow: The fluorescence intensity of S1 and S2 compositions was not uniformly distributed in the entire vascular system, with a more intense fluorescence activity or flow stasis in the blood vessels near the injection site. This phenomenon was not observed in the compositions with a higher squalene % (S3 and S4 compositions), which demonstrated blood flow of the blood vessels at different depths and organs. Without being bound by any particular theory, it is believed the stasis flow of S1 and S2 compositions is due to a higher percentage of solidified fat, such as cetyl palmitate, Precirol®, and Compritol®.

The fluorescence activity of the DiR control solution was distributed in the entire vascular system, including the microvasculatures and the lymphatic system. Compare to ICG and S1-S4 compositions, more DiR control solution was distributed into and provided a better delineation of the microvasculature (for example, capillary). In addition, only DiR control solution (not S1-S4 compositions) entered into the lymphatic system and allowed the optical system of the lymphatic system.

The available imaging times for the DiR control solution and S1-S4 compositions were longer than that of FDA approved fluorescence dye, ICG (about 5 minutes). The imaging time for S3 and S4 solutions was about 60 minutes or more. The imaging time for microvasculature and lymphatic system, using DiR control solution, was between 120 to 240 minutes after IV DiR dye injection.

ICG was more rapidly cleared by the liver (within 5 minutes post injection) compare to the control DiR solution (30-120 minutes post injection) and S1-S4 compositions (30-120 minutes post injection).

These results suggest the DiR control solutions a better contrast agent for optical imaging the microvasculature and the lymphatic system, whereas S1-S4 compositions can be used for imaging the small and large blood vessels. In addition, compositions with a higher squalene % (i.e., S3 and S4 compositions) provide a superior delineation of the fluorescence signal and blood flow at different depths.

After the in vivo imaging, the organs were isolated from the rats. The isolated organs showed a more intense fluorescence activity compared to those in the in vivo condition.

Fluorescence Activity in the Skin: fluorescence activity was detected in skin 4 hours after the injection of the compositions and the control solution. The control group showed a strongest fluorescence activity in the skin, followed by S4 composition. Although S4 composition showed fluorescence activity in skin microvasculature, this signal was not detected during in vivo imaging.

Fluorescence Activity in the Muscle Underneath the Skin: The strongest fluorescence signal was observed in rats injected with S1 and S2 compositions. The rats injected with the control solution also showed an intense fluorescence activity.

Fluorescence Activity in Heart, Lungs, Liver, Spleen, and Kidneys: For rats injected with S1 and S2 compositions, the highest level of fluorescence was detected in liver, followed by spleen, kidneys, heart, and lungs. The rats injected with compositions with a higher squalene % (i.e., S3 and S4 compositions) showed a reduction of fluorescence signal in all of the isolated organs. The DiR control group showed fluorescence activity in the liver and spleen.

A high fluorescence signal in kidneys of the control group was noted. This result indicates non-encapsulated DiR molecules in the control solution are smaller than that of the nanoparticles in S1-S4 compositions, and the small-sized DiR molecules favored a renal clearance.

Figure 5:
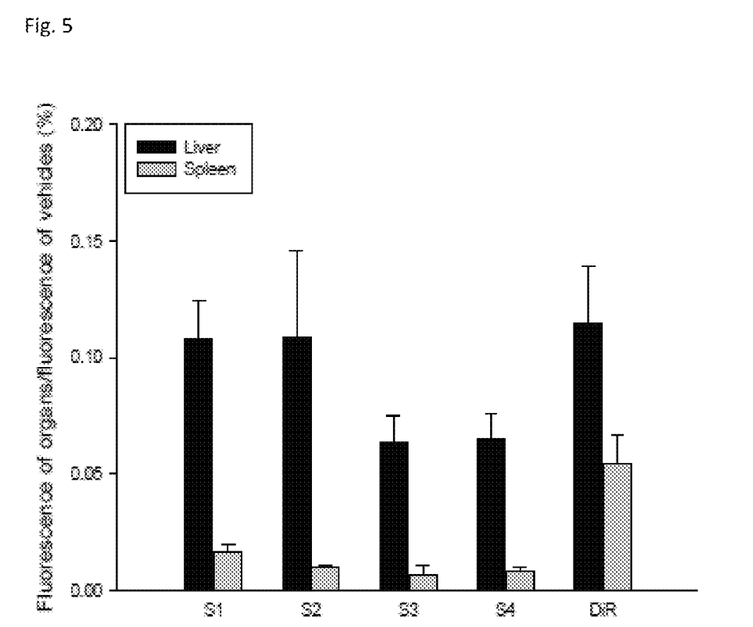
FIG. 5 is a bar graph illustrating the fluorescence emission of the liver and spleen of rats injected with S1-S4 compositions and the DiR control solution (DiR).

FIG. 5 illustrates a relatively high accumulation of the fluorescence signals in the liver for S1-S4 compositions and the DiR control group, although the signals in the liver were lower in the S3 and S4 compositions.

Referring to FIG. 5, the fluorescence signals were detected in the spleen in all study groups, although the signals were less in S1-S4 compositions compare to the DiR control group. These results show a lower uptake and lower accumulation of S1-S4 compositions by the reticulo-endothelial system (RES), especially in compositions with a lower % of triterpene and a higher % of CP (i.e., S1 and S2). Without being bind by any particular theory, this can be due to the lipophilic nature of S1 and S2 compositions, which are cleared faster in the circulation compared to hydrophilic compositions. The log P of CP (fatty ester) and squalene (triterpene) are 14.61 and 10.68, respectively. S1 and S2 compositions with a higher % of CP are more lipophilic, resulting in a faster clearance from the circulation.

Example 7: Optical Imaging of Organ Sections

Additional blood flow optical imaging of the resected muscle and liver was performed. The fluorescence signal was seen predominantly in the muscle capillary after administering S3 solution and the control solution. A negligible fluorescence signal was detected in the areas surrounding the muscle capillary. For rats injected with S4 solution, the fluorescence activity was seen over the endothelial wall of the blood vessel, indicating adhesion of the nanoparticles to the endothelial walls. This adhesion did not produce an uneven distribution of the fluorescence signal during blood flow imaging.

In rats injected with S3 and S4 compositions, the fluorescence signal in the liver was predominant intravascular (i.e. within the blood vessel lumen). For the DiR control group, the fluorescence signals accumulated in the liver capillary and outside the liver vasculature (extravasation from the blood vessel lumen into interstitial spaces).

Figure 6A:
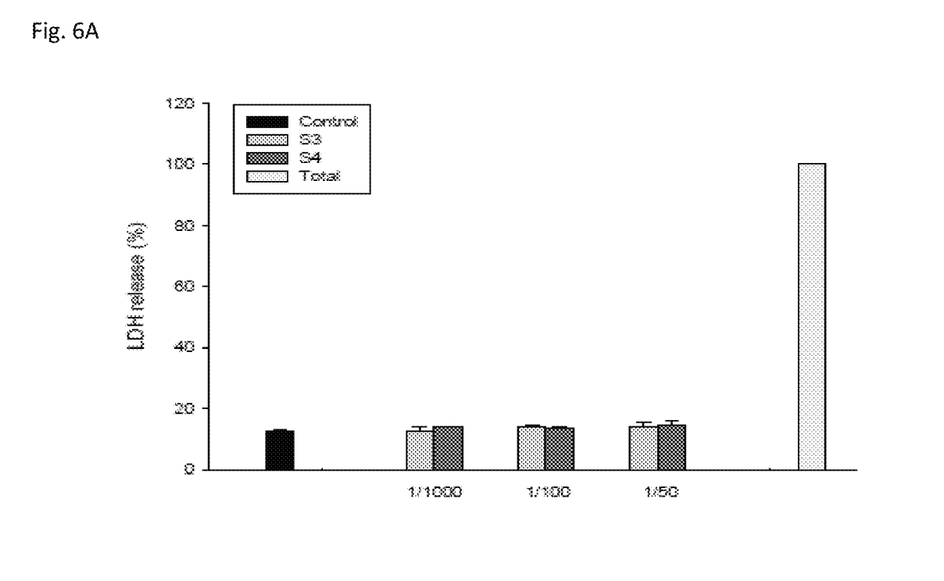
FIG. 6A is a bar graph showing the % of lactate dehydrogenase (LDH) release from neutrophils incubated with S3 and S4 compositions, and the control solution.

Example 8: Cytotoxicity and Biocompatibility Evaluation of S3 and S4 Compositions The cytotoxicity of S3 and S4 compositions was evaluated using LDH assay and HUVECs. Neutrophil cytotoxicity is manifested by LDH release from damaged cells. About 13% LDH release was noted after incubation of human neutrophils with the control solution. Incubating human neutrophils with S3 and S4 compositions, at various concentrations (1/1000. 1/100 and 1/50), lead to a comparable LDH release % (about 15%) as compared to the control group (about 15%), as illustrated in FIG. 6A. The results show S3 and S4 compositions are safe compare to the control solution.

Figure 6B:
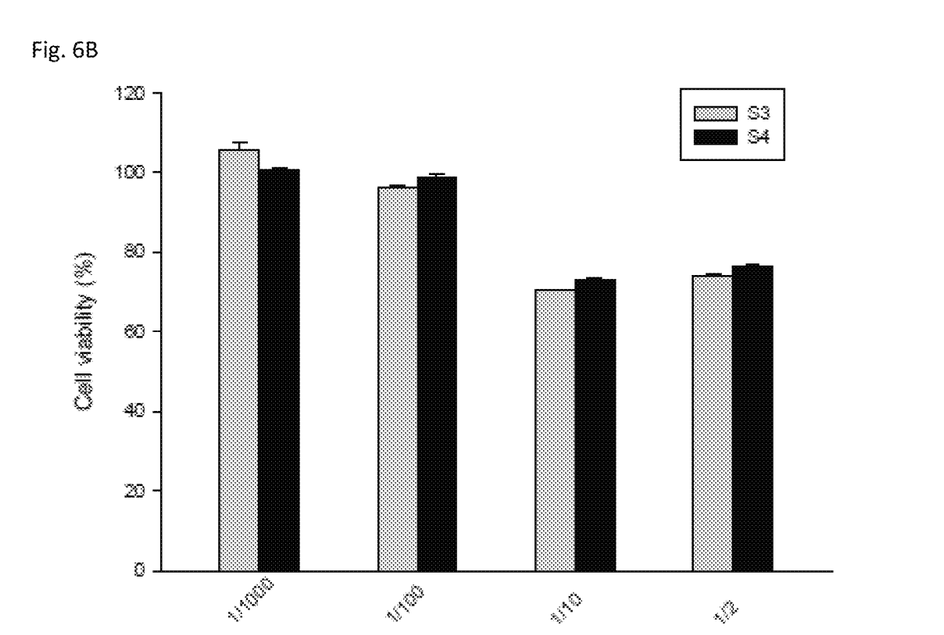
FIG. 6B is a bar graph showing the % of human umbilical vein endothelial cells (HUVEC) viability at different concentrations of S3 and S4 compositions.

The biocompatibility of S3 and S4 compositions was evaluated using HUVECs. As shown in FIG. 6B, HUVEC viability was above 90% at the concentrations of 1/1000 and 1/100, and about 70% at concentrations of 1/10 and 1/2. No difference of cell viability ($p>0.05$) was detected between S3 and S4 compositions.

What is claimed is:

1. A composition, comprising:
   one or more nanoparticles, comprising:
     squalene;
     cetyl palmitate;
     soy phosphatidylcholine (SPC); and
     carbocyanine,
     wherein the composition comprises about 8%-10% squalene (v/w), less than 2% cetyl palmitate (v/w), about 0.2% (v/w) SPC, and about 0.005% (v/w) carbocyanine.

2. The composition of claim 1, wherein said carbocyanine is 1'-Dioctadecyl-3,3,3',3'-tetramethyl-indotricarbocyanine iodide (DiR).

3. The composition of claim 1, wherein the nanoparticle further comprises one or more surface additives selected from distearoylphosphatidylethanolamine-polyethylene glycol (DSPE-PEG), Myverol, or Pluronic F68.

4. The composition of claim 3, wherein the nanoparticle comprises about 0.2% (v/w) of DSPE-PEG, about 0.5% (v/w) Myverol, and 5% (v/w) Pluronic F68.

5. The composition of claim 1, further comprises a therapeutic agent.

6. The composition of claim 1, further comprises a ligand.

7. A composition, comprising
   one or more nanoparticles, comprising:
     squalene;
     cetyl palmitate;
     one or more surface additives selected from soy phosphatidylcholine (SPC), distearoylphosphatidylethanolamine-polyethylene glycol (DSPE-PEG), Myverol, and Pluronic F68; and 1'-Dioctadecyl-3,3,3',3'-tetramethyl-indotricarbocyanine iodide (DiR),
wherein the composition comprises about 0.005% (v/w) DiR, about 8%-10% squalene (v/w), and less than 2% cetyl palmitate (v/w).

8. A method for performing a diagnostic procedure comprising administering to a subject an effective amount of the composition of claim 1.

9. The method of claim 8, wherein the diagnostic procedure is optical imaging.

10. The method of claim 8, wherein the optical imaging is by fluorescence method.

11. The method of claim 9, wherein the optical imaging uses a wavelength in the region of about 380 to about 1000 nm.

12. The method of claim 9, wherein the optical imaging uses a wavelength in the region of about 700 to about 900 nm.

13. The composition of claim 7, wherein the nanoparticle comprises about 0.2% SPC (v/w), about 0.2% (v/w) of DSPE-PEG, about 0.5% (v/w) Myverol, and about 5% (v/w) Pluronic F68.

* * * * *